(12) United States Patent
Shibata et al.

(10) Patent No.: US 11,021,588 B2
(45) Date of Patent: Jun. 1, 2021

(54) METHOD FOR PRODUCING POROUS CELLULOSE MEDIUM

(71) Applicant: DAICEL CORPORATION, Osaka (JP)

(72) Inventors: Toru Shibata, Himeji (JP); Yasuto Morishita, Himeji (JP); Yosuke Ito, Himeji (JP)

(73) Assignee: DAICEL CORPORATION, Osaka (JP)

( * ) Notice: Subject to any disclaimer, the term of this patent is extended or adjusted under 35 U.S.C. 154(b) by 450 days.

(21) Appl. No.: 15/327,940

(22) PCT Filed: Jul. 22, 2015

(86) PCT No.: PCT/JP2015/070797
§ 371 (c)(1),
(2) Date: Jan. 20, 2017

(87) PCT Pub. No.: WO2016/013568
PCT Pub. Date: Jan. 28, 2016

(65) Prior Publication Data
US 2017/0210871 A1    Jul. 27, 2017

(30) Foreign Application Priority Data
Jul. 22, 2014    (JP) .............................. JP2014-148930

(51) Int. Cl.
C08J 9/26          (2006.01)
C08J 3/16          (2006.01)
(Continued)

(52) U.S. Cl.
CPC ............ C08J 9/26 (2013.01); B01D 15/3809 (2013.01); B01J 20/24 (2013.01); B01J 20/285 (2013.01);
(Continued)

(58) Field of Classification Search
CPC .... C08J 9/26; B01D 15/3809; B01D 15/3804; B01J 20/24; B01J 20/28016;
(Continued)

(56) References Cited

U.S. PATENT DOCUMENTS 4,063,017 A    12/1977  Tsao et al.
4,090,022 A    5/1978   Tsao et al.
(Continued)

FOREIGN PATENT DOCUMENTS

EP    2626381 A1    8/2013
EP    2 818 500 A2  12/2014
(Continued)

OTHER PUBLICATIONS

Extended European Search Report issued in corresponding European Application No. 15824809.6 and dated Mar. 21, 2018.
(Continued)

Primary Examiner — Katherine Zalasky McDonald
(74) Attorney, Agent, or Firm — Birch, Stewart, Kolasch & Birch, LLP (57) ABSTRACT

The present invention provides a technique for preparing a porous cellulose medium, through the gelation of a solution in which cellulose acetate as a raw material is dissolved, which does not cause a reaction involving the migration of substances. Specifically, a method for producing a porous cellulose medium is provided which includes the steps of gelling a flowable homogeneous composition containing cellulose acetate, an organic solvent, and water through a decrease in temperature; and hydrolyzing the cellulose acetate contained in the resulting gel.

11 Claims, 5 Drawing Sheets

(51) Int. Cl.
*B01J 20/28* (2006.01)
*B01J 20/30* (2006.01)
*B01J 20/285* (2006.01)
*B01J 20/24* (2006.01)
*C08J 3/075* (2006.01)
*B01J 20/32* (2006.01)
*B01J 20/286* (2006.01)
*B01D 15/38* (2006.01)
*C07K 1/22* (2006.01)
*C07K 16/00* (2006.01)

(52) U.S. Cl.
CPC ....... *B01J 20/286* (2013.01); *B01J 20/28019* (2013.01); *B01J 20/28042* (2013.01); *B01J 20/3007* (2013.01); *B01J 20/3078* (2013.01); *B01J 20/3212* (2013.01); *B01J 20/3274* (2013.01); *C07K 1/22* (2013.01); *C07K 16/00* (2013.01); *C08J 3/075* (2013.01); *C08J 3/16* (2013.01); *C08J 2301/12* (2013.01)

(58) Field of Classification Search
CPC .................. B01J 20/28033; B01J 20/28; B01J 20/28042; B01J 20/285; B01J 20/286; B01J 20/3007; B01J 20/3078; B01J 20/3208; B01J 20/3212; B01J 20/3242; B01J 20/3274; B01J 20/291
See application file for complete search history.

(56) References Cited

U.S. PATENT DOCUMENTS

| 4,118,449 | A | 10/1978 | Rinde |
| 4,663,447 | A | 5/1987 | Yamazaki et al. |
| 5,108,596 | A | 4/1992 | Ookuma et al. |
| 5,196,527 | A | 3/1993 | Ookuma et al. |
| 5,723,601 | A * | 3/1998 | Larsson ............... B01D 67/003 210/635 |
| 2003/0038081 | A1* | 2/2003 | Wang ................... B01D 61/145 210/651 |
| 2016/0200835 | A1* | 7/2016 | Kurabayashi ............. C08B 3/06 536/71 |

FOREIGN PATENT DOCUMENTS

| EP | 3 042 925 A1 | 7/2016 |
| JP | 52-129788 A | 10/1977 |
| JP | 60-155245 A | 8/1985 |
| JP | 62-277401 A | 12/1987 |
| JP | 63-95237 A | 4/1988 |
| JP | 1-254256 A | 10/1989 |
| JP | 2-208330 A | 8/1990 |
| JP | 6-254373 A | 9/1994 |
| WO | WO93/19115 A1 | 9/1993 |
| WO | WO 02/053598 A2 | 7/2002 |

OTHER PUBLICATIONS

Bai et al., "Preparation and characterization of crosslinked porous cellulose beads", Carbohydrate Polymers, 2006, vol. 64, pp. 402-407.
Chen et al. "Physical Characteristics of Porous Cellulose Beads as Supporting Material for Immobilized Enzymes", Biotechnology and Bioengineerning, 1976, vol. 18, pp. 1507-1516.
International Search Report for PCT/JP2015/070797 dated Oct. 27, 2015.
Reuvers et al., "Demixing and Gelation Behavior of Ternary Cellulose Acetate Solutions", Journal of Polymer Science, 1986, vol. 24, pp. 793-804.
Written Opinion of the International Searching Authority for PCT/JP2015/070797 (PCT/ISA/237) dated Oct. 27, 2015.
Chinese Office Action for Application No. 201580040297.7, dated Jan. 9, 2020, with English language translation.

\* cited by examiner

METHOD FOR PRODUCING POROUS CELLULOSE MEDIUM

TECHNICAL FIELD

The present invention relates to a method for producing a porous cellulose medium.

BACKGROUND ART

Polysaccharides represented by cellulose and derivatives thereof are used for a variety of applications. These microporous materials per se can serve as adsorbents, or when these microporous materials undergo a certain chemical modification on their surface, they can be provided with a function such as adsorption or separation.

One of such examples will now be described. Along with the prevalence of enzyme utilization or the development of biopharmaceuticals, the separation and purification of biopolymers such as proteins have become one of the important technical issues. Chromatography is an important means for solving this issue. Chromatography uses a separating agent in which a certain atomic group (often referred to as a selector) that interacts with an intended material or an impurity to be removed has been bound to a solid referred to as a matrix.

An extremely important property of a material for separating a biopolymer is that it does not non-specifically adsorb proteins, and therefore, polysaccharides are valued for use as the matrix. Moreover, the presence of a large number of hydroxyl groups in the molecules of polysaccharides allows the selector to be readily bound via ether linkages or ester linkages using the hydroxyl groups as a scaffold, which is also an important factor that makes polysaccharides valued for use as the matrix.

For the separation and purification of a biopolymer, generally, a method is used in which the matrix is bound with a selector having a certain affinity for an intended molecule, and after the adsorption of the intended molecule, the adsorbed intended molecule is liberated and collected in a certain manner. In order to obtain a large amount of the intended molecule, the matrix is demanded to have a porous structure that allows a large amount of the selector to be bound, and also allows free entry and exit of the intended molecule, in order to allow the selector and the biopolymer having a high molecular weight to be efficiently interacted with each other. In other words, when the matrix is packed into a column to perform size exclusion chromatography, the matrix needs to exhibit an exclusion limit greater than the combined size of the molecule to be purified and the ligand.

This matrix is typically used by being packed as particles into a tube referred to as a column. In recent years, however, attention has been drawn to a new form referred to as a monolith, which is an integral porous material. This is used for the same application by being contained in a container such as a small tube referred to as a capillary, or a column. The monolith, however, can also be used as a filtration membrane, if it has a relatively small thickness and a large area.

One factor for the ease of use of this matrix is the physical strength, in addition to the selectivity for the target to be separated. Specifically, when a liquid or gas is passed during chromatography or filtration, a matrix having a low elastic modulus will undergo compressive deformation or breakage, and as a result, the flow of the liquid within the chromatographic column will become uneven, or even clogging will occur, leading to a significant deterioration in the separation efficiency of the column. In view of this, high physical strength is an important property, and in this respect, cellulose is an outstanding material among polysaccharides.

Additionally, cellulose has alcoholic hydroxyl groups on the surface as a general characteristic of polysaccharides, and thus, has advantages in that, for example, it is capable of binding a variety of atomic groups by chemical reactions, or is available in abundance and at relatively low cost in the form of a highly pure raw material.

For the foregoing reasons, porous cellulose particles for the main purpose of separating and purifying biopolymers have been developed. Among methods for producing such porous cellulose particles, many methods involve dissolving cellulose in a certain manner, followed by regeneration, while some methods use organic acid esters as starting materials. Direct dissolution of cellulose per se can be difficult in that a special solvent is required, or the viscosity of the solution is very high. On the other hand, the methods using organic acid esters as starting materials utilize the following advantages, for example: organic acid esters can be dissolved in many solvents; organic acid esters of cellulose are industrially supplied with stable quality, at various binding rates or degrees of polymerization with various organic acids; and the ester linkages can be readily broken down to regenerate cellulose.

Patent Literature 1, for example, describes a method for producing such cellulose particles, which includes dispersing, in an aqueous medium, a solution of a cellulose organic acid ester dissolved in an organic solvent such as a halogenated hydrocarbon to form microdroplets of the ester solution, and adding a hydrolysis accelerator such as an ammonium salt thereto to cause hydrolysis of the ester, thus forming cellulose microparticles.

Patent Literature 2 describes a method for producing porous spherical particles, which includes dissolving, in an organic solvent, a cellulose fatty acid ester and a gelling agent for the cellulose fatty acid ester to form a solution, adding the solution into an aqueous medium under stirring to form droplets, further adding a coagulation accelerator to convert the cellulose fatty acid ester contained in the droplets into gel particles, and removing the gelling agent, coagulation accelerator, and solvent from the resulting particles.

Non Patent Literature 1 describes that porous particles are formed by dissolving cellulose acetate in a water-soluble organic solvent (a mixed solvent of acetone and DMSO), and dispersing the solution in water, which causes the solution containing cellulose acetate to coagulate upon contact with water.

Non Patent Literature 2 describes that cellulose particles (beads) are obtained by dissolving cellulose diacetate in DMSO, subsequently adding anhydrous sodium sulfate and stirring the mixture, and introducing the mixture into an acid coagulating bath (hydrochloric acid). Moreover, a means for increasing the porosity of the beads by immersing extracted beads in a large amount of warm water to remove sodium sulfate is described.

CITATION LIST

Patent Literature

Patent Literature 1: Japanese Patent Laid-Open No. 62-277401
Patent Literature 2: Japanese Patent Laid-Open No. 63-95237

Non Patent Literature

Non Patent Literature 1: Chen, L. F.; Tsao, G. T. Biotechnol. Bioeng. 1976, 18, 1507
Non Patent Literature 2: Bai, Y.-X.; Li, Y.-F. Carbohydr. Polym. 2006, 64, 402
Non Patent Literature 3: A. J. Reuvers et al., J. Polym. Sci., 1986, 24, 793

DISCLOSURE OF INVENTION

Technical Problem

According to the techniques described in Patent Literatures 1 and 2, a solvent containing a halogenated hydrocarbon is used in both methods, and during the preparation of the particles, the solvent is removed by vaporization, which requires a large amount of energy and an apparatus for collecting the vaporized solvent. Moreover, when the coagulation accelerator as described in Patent Literature 2 is used, a dense layer of the cellulose fatty acid ester may form in the portion of contact with the coagulation accelerator in the formed droplets, possibly resulting in a distorted particle shape. Further, the use of a process that involves the migration of substances as described in Patent Literature 2 may produce a nonuniform reaction.

Moreover, Non Patent Literature 1 describes cross-linking the beads by subjecting the formed beads to a cross-linking reaction using formaldehyde and hydrochloric acid, and Non Patent Literature 2 describes using a pore forming agent for providing the particles with pores. In both cases, the step of treating the surface during the formation of the particles is included, and the removal of the substances used for the surface treatment is required to obtain the porous cellulose particles.

An object of the present invention is to provide a technique for preparing a porous cellulose medium applicable to a separating agent, by obtaining porous cellulose acetate by gelling a homogeneous composition containing cellulose acetate as a raw material, water, and an organic solvent, without causing the migration of substances out of the system, and then hydrolyzing the porous cellulose acetate.

Solution to Problem

The present invention was made in view of the foregoing circumstances. It has been reported in a paper that a homogeneous composition containing water, an organic solvent, and cellulose acetate undergoes a phase transition (liquid-gel) at a certain temperature or lower to form a gel (Non Patent Literature 3).

The present inventors found that by utilizing this property, a gel having a shape suitable for the purpose, such as a mass shape or a particulate shape, can be obtained for the above-described composition without causing the migration of substances, for example, without evaporating the solvent or adding a non-solvent (gelling agent), and the gel can then be hydrolyzed to obtain a cellulose medium having excellent characteristics in which the porous structure is maintained.

A summary of the present invention is as set forth below.

[1] A method for producing a porous cellulose medium including the steps of:
gelling a flowable homogeneous composition containing cellulose acetate, an organic solvent, and water through a decrease in temperature; and
hydrolyzing the cellulose acetate contained in the resulting gel.

[2] A method for producing spherical porous cellulose particles including:
a first step of obtaining a dispersion by dispersing a flowable homogeneous composition containing cellulose acetate, an organic solvent, and water in a dispersion medium not miscible with the homogeneous composition;
a second step of forming gelled particles composed of the composition by gelling the composition by reducing a temperature of the resulting dispersion; and
a third step of hydrolyzing the cellulose acetate contained in the resulting gelled particles.

[3] The method for producing spherical porous cellulose particles according to [2], which includes, between the second step and the third step, the step of adding a separating solvent for separating the resulting gelled particles, into the dispersion in which the gelled particles are formed, thereby separating the gelled particles into the separating solvent.

[4] The method for producing spherical porous cellulose particles according to [3], wherein the separating solvent is water, methanol, ethanol, 2-propanol, acetamide, formamide, or a mixture thereof.

[5] The method for producing spherical porous cellulose particles according to any one of [2] to [4], wherein a dispersion stabilizer is added into the dispersion medium.

[6] The method according to any of [2] to [5], wherein the dispersion medium is a hydrocarbon having 20 or more carbon atoms, a silicone oil, or a fluorinated hydrocarbon.

[7] A method for producing a porous cellulose monolith including the steps of:
placing a flowable homogeneous composition containing cellulose acetate, an organic solvent, and water in a mold container, and gelling the homogeneous composition within the mold container through a decrease in temperature; and
hydrolyzing the cellulose acetate contained in the resulting gel.

[8] The method according to any of [1] to [7], wherein the organic solvent contained in the homogeneous composition has a boiling point of 120° C. or higher, and is miscible with water, but is not miscible with a saturated hydrocarbon.

[9] The method according to any of [1] to [8], wherein the organic solvent contained in the homogeneous composition is an aprotic polar solvent.

[10] The method according to any of [1] to [9], wherein the homogeneous composition has, in a range of temperatures from 0° C. to 100° C., a temperature range where the homogeneous composition is a transparent flowable liquid, and a phase transition temperature at which the homogeneous composition loses flowability at a temperature lower than the temperature range.

[11] The method according to any of [1] to [10], wherein the cellulose acetate is one or more selected from the group consisting of cellulose diacetate and cellulose monoacetate.

[12] A method for producing an adsorbent including the step of immobilizing an affinity ligand onto the porous cellulose medium obtained using the method according to [1], the porous cellulose particles obtained using the method according to any of [2] to [6], or the porous cellulose monolith obtained using the method according to [7].

[13] The method for producing an adsorbent according to [12], wherein the affinity ligand is one or more selected from the group consisting of protein A, protein G, protein L, and a functional variant thereof.

[14] A method for purifying a target substance including:
a first step of contacting the adsorbent obtained using the method according to [12] or [13] with a mixture containing the target substance to allow the target substance to bind to the affinity ligand immobilized onto the adsorbent; and a second step of separating the target substance bound to the affinity ligand on the adsorbent.

Advantageous Effects of Invention

According to the present invention, in the production of a porous cellulose medium such as porous cellulose particles, there is no need to use an organic chlorine-based solvent such as a halogenated hydrocarbon for dissolving cellulose acetate, and moreover, gelation caused by a change in temperature, which does not involve the migration of substances, is utilized in the gelation of the composition containing cellulose acetate, which allows the size of the pores of the obtained cellulose acetate medium to be uniform.

DESCRIPTION OF EMBODIMENTS

The method for producing a porous cellulose medium according to the present invention utilizes the property of a homogeneous composition containing cellulose acetate, an organic solvent, and water to undergo a phase transition from liquid to gel through a change in temperature, and involves forming a gel composed of the homogeneous composition through a change in temperature, and subsequently converting the cellulose acetate contained in the gel into cellulose by hydrolysis.

In the present invention, the phase transition from liquid to gel through a change in temperature is a phenomenon in which a liquid composition having flowability at a certain temperature loses its flowability upon a change in temperature. For example, the phenomenon in which a decrease in temperature results in an increase in viscosity is observed in many homogeneous solution compositions, and when a liquid turns into a gel, it completely loses its flowability, and often becomes cloudy.

In the present invention, gelation is induced by a change in temperature, without the addition of a reagent for inducing gelation, for example.

<Cellulose Acetate>

Cellulose acetate used in the present invention may be any cellulose acetate as long as a composition containing water, an organic solvent, and the cellulose acetate undergoes the phase transition depending on the temperature.

Physical properties of cellulose acetate may be represented by the degree of polymerization and the degree of substitution, for example.

The degree of polymerization is preferably 50 or more as the weight average, in order to increase the mechanical strength of the resulting porous cellulose particles, and prevent the elution thereof into the solvent or the like during use. On the other hand, with regard to the upper limit of the degree of polymerization, any commercially available cellulose acetate can be used.

The degree of substitution has a strong effect on the solubility of cellulose acetate.

The degree of substitution refers to a numerical value indicating the number of substituted hydroxyl groups out of the three hydroxyl groups per glucose residue in cellulose, and in the case of an acetate, the degree of substitution may be expressed in terms of acetic acid content or acetyl group content; however, these values can be converted between each other. Generally, cellulose acetate having a degree of substitution around 2.8 to 2.9 is distributed as triacetate, and cellulose acetate having a degree of substitution around 2.5 is distributed as diacetate. In the present invention, cellulose acetate having any degree of substitution may be used as long as it provides a composition that undergoes the phase transition. The degree of substitution refers to the average value of the number of hydroxyl groups replaced with other substituents, out of the three hydroxyl groups per glucose residue in cellulose.

Cellulose acetate that is commonly distributed is available in the following forms: so-called cellulose diacetate used for general purposes such as textile materials (in particular, a typical product has a degree of substitution of acetyl groups of 2.5, and is represented by an acetic acid content (degree of acetylation) around 55%); and cellulose triacetate used as film materials for pictures or liquid crystal displays (having a degree of substitution of acetyl groups of 2.8 to 2.9, and represented by an acetic acid content (degree of acetylation) around 60%). Cellulose acetate having a degree of substitution around 1 (although such cellulose acetate should be referred to as monoacetate, since it is not commonly distributed, the name "monoacetate" has not been established as a common name) may even dissolve in water, and has a wide range of options for polar solvent systems. Such cellulose acetate of a grade that is not commonly distributed can be obtained, for example, by adding a calculated amount of a base into a solution of cellulose acetate having a higher degree of substitution to perform solvolysis, or by hydrolyzing a hydrous acetic acid solution of the cellulose acetate using an acid catalyst such as sulfuric acid, and stopping the reaction at an appropriate time (neutralizing the sulfuric acid). For example, the above-described cellulose acetate can be obtained by reacting diacetate (cellulose diacetate) as a starting material with 1.5 equivalents of a base per glucose unit. As the base, hydrazine or hydroxylamine is easy to use because they are neutral molecules and thus, are readily miscible with many organic solvents, and are fast to react. That is, any base that is miscible with the raw material solution can be used, for example, a hydroxide such as a quaternary ammonium hydroxide.

While the boundary between triacetate, diacetate, and monoacetate in terms of the degree of acetylation is not clearly defined, in the present invention, triacetate is defined as having a degree of acetylation of 2.7 or more, diacetate is defined as having a degree of acetylation of 1.5 or more and less than 2.7, and monoacetate is defined as having a degree of acetylation of 0.5 or more and less than 1.5, for convenience sake.

<Composition in the Present Invention>

The composition used in the method of the present invention is the homogeneous composition containing cellulose acetate, an organic solvent, and water described above. The homogeneous composition refers to the composition in which water, the organic solvent, and cellulose acetate are homogeneously mixed.

In the present invention, the phase transition from liquid to gel that occurs through a change in temperature is a phenomenon in which a liquid composition having flowability at a certain temperature loses its flowability upon a change in temperature.

In the present invention, the temperature at which the phase transition from liquid to gel occurs can be adjusted by appropriately changing the composition of this composition or the degree of polymerization or the degree of substitution of the cellulose acetate to be incorporated.

The homogeneous composition preferably has, in a range of temperatures from 0° C. to 100° C., a temperature range where the homogeneous composition is a transparent flowable liquid, and a phase transition temperature at which the homogeneous composition loses its flowability at a temperature lower than the temperature range.

The contents of cellulose acetate, the organic solvent, and water in the above-described composition may be any as long as the composition undergoes the phase transition in a predetermined range of temperatures.

The content of cellulose acetate in the composition is preferably 1 to 20 wt %, and more preferably 5 to 15 wt %, in order to provide the resulting porous cellulose with a pore size suitable for practical use and an appropriate hardness.

As the ratio of water to the organic solvent incorporated in the above-described composition, any ratio that can cause gelation may be adopted. For example, in an exemplary embodiment, the ratio by weight of water to the organic solvent may be 10:90 to 90:10.

The type of the organic solvent and the composition ratio by weight of water to the organic solvent in the above-described composition used in the method of the present invention may be any as long as the composition undergoes the phase transition as described above. As reported in Non Patent Literature 3 listed above, the acetone/water mixture system for CDA, as well as the dioxane/water mixture system may be used. These organic solvents, however, are difficult to handle in that, because considerable amounts of these organic solvents dissolve into liquid paraffins, or the vapor pressures of these organic solvents are high, they tend to cause unexpected gelation due to the migration of substances caused by factors other than the temperature in the course of the dispersion process. Desirably, therefore, the organic solvent has low solubility in nonpolar liquids such as liquid paraffins, and is unlikely to undergo a change in concentration due to evaporation. Preferred as organic solvents having such attributes are those that are not homogeneously miscible with a saturated hydrocarbon such as hexane, and have boiling points of 120° C. or higher.

Solvents having high dissolving power for cellulose acetate in general and having the above-described properties include many aprotic polar solvents, for example, one or more selected from DMSO, sulfolane, dimethylsulfone, N-methylpyrrolidone, N,N-dimethylacetamide, N,N'-dimethylimidazolidinone, hexamethylphosphoric triamide, and tetramethylurea.

Examples of the actual composition may be described as follows.

[Exemplary Composition Using Cellulose Monoacetate]

A composition containing 5 wt % of cellulose monoacetate, 55 wt % of water, and 45 wt % of DMSO shows a transparent and viscous liquid at a temperature higher than around 55° C., and forms a cloudy gel at temperatures lower than this temperature. Note that this conversion is reversible.

[Exemplary Compositions Using Cellulose Diacetate]

A composition containing 5 wt % of cellulose diacetate, 20 wt % of water, and 80 wt % of DMSO is liquid at 70° C. or higher, and forms a gel at 50° C. or lower. Note that this change is reversible.

A composition containing 6.8 wt % of cellulose diacetate, 71.6 wt % of NMP (N-methylpyrrolidone), and 21.6 wt % of water is a gel at 20° C. or lower, and is a transparent liquid at 40° C. or higher. Note that this change is reversible.

A composition containing 7.7 wt % of cellulose diacetate, 73.7 wt % of N,N-dimethylacetamide, and 18.6 wt % of water is a gel at 20° C. or lower, and is a transparent liquid at 50° C. or higher. Note that this change is reversible.

Generally, the above-described temperature at which the phase transition occurs decreases as the proportion of the organic solvent increases, and increases as the proportion of water increases.

The phase transition temperature is preferably 0° C. to 100° C., and more preferably 30 to 70° C., in view of handleability in the production of the porous cellulose medium.

<Hydrolysis>

In the resulting gel composed of the homogeneous composition containing cellulose acetate, the cellulose acetate contained in the gel is converted into highly hydrophilic cellulose by hydrolysis. For this purpose, the acetyl groups in the cellulose acetate are removed.

The acetyl groups can be removed by the reaction with a metal hydroxide (such as sodium hydroxide or caustic potash), a quaternary ammonium hydroxide, barium hydroxide, calcium hydroxide, or the like. An amine can also be used in the reaction for removing the acetyl groups. Examples of amines include ammonia, hydrazine, hydroxylamine, guanidine, and alkylamines.

The reaction conditions cannot be uniquely determined because the above-described compounds have different solubilities and reaction rates for the solvent. A known method can be used, and the acetyl groups may be removed to a level suitable for the purpose of use.

After the completion of the reaction, the resulting porous cellulose is washed with a solvent that does not adversely affect the porous cellulose, and a preservative is optionally added.

<Shape of the Porous Cellulose Medium>

The porous cellulose medium produced using the method of the present invention can be used either as spherical particles or a monolith.

In the preparation of the spherical particles or monolith, the process for controlling the shape is different, although there is no essential difference in the process of gelling the above-described specific composition by reducing the temperature of the composition, and then hydrolyzing the cellulose acetate contained in the resulting gel. For the production of the monolith, the above-described homogeneous composition is caused to undergo the phase transition in a container having a desired shape. On the other hand, for the production of the particles, generally, the homogeneous composition as a solution is caused to undergo a change in temperature while being dispersed in a dispersion medium not miscible with the homogeneous composition, to undergo the phase transition. Specific methods for producing the monolith and for producing the spherical particles will be briefly described hereinafter.

<Spherical Particles>

An exemplary embodiment of the method for producing spherical porous cellulose particles of the present invention may be a method including a first step of obtaining a dispersion by dispersing a flowable homogeneous composition containing cellulose acetate, an organic solvent, and water in a dispersion medium not miscible with the homogeneous composition; a second step of forming gelled particles composed of the composition by gelling the composition by reducing a temperature of the resulting dispersion; and hydrolyzing the cellulose acetate contained in the resulting gelled particles.

The method may further include, between the second step and the third step, the step of adding a separating solvent for separating the resulting gelled particles, into the dispersion in which the gelled particles are formed, thereby separating the gelled particles into the separating solvent.

In the method for producing spherical porous cellulose particles of the present invention, a dispersion medium for dispersing the above-described composition is used. Any dispersion medium may be used in the present invention as long as it is not miscible with water and the organic solvent contained in the composition to cause unintentional gelation or an extreme change in the phase transition temperature of the composition, which may adversely affect the pore size of the intended spherical porous cellulose particles.

In order to prevent aggregation of the composition during dispersion of the composition, the dispersion medium preferably has a certain degree of viscosity during the dispersion of the composition.

The viscosity of the dispersion medium may be 0.2 to 20 Pa·S at 25° C., for example.

The dispersion medium is preferably a nonpolar dispersion medium so that it is not miscible with water and the organic solvent contained in the above-described composition. Examples of such nonpolar dispersion media include hydrocarbons having 20 or more carbon atoms such as liquid paraffins and petrolatum, silicone oils, and fluorinated hydrocarbons.

Petrolatum is effective for the purpose of increasing the yield of the particles. Petrolatum rapidly loses its flowability once the temperature is reduced below a specific softening temperature. Therefore, when the particles of the dispersed liquid to make gel tend to aggregate into a mass, the dispersion may be prepared first at the softening temperature or higher, and then the dispersion may be cooled below the softening temperature, so as to prevent migration and contact of droplets to form gel. The softening temperature of petrolatum differs depending on the type, and may be selected as appropriate.

After being dispersed in the dispersion medium, the composition containing cellulose acetate of the present invention needs to maintain its dispersed state until it is gelled by reducing the temperature of the composition. For this purpose, it is preferred to add an appropriate dispersion stabilizer into the dispersion medium.

The dispersion stabilizer may be any dispersion stabilizer effective at increasing the stability of the dispersed state of the composition, and reducing the rate of aggregation of the particles composed of the composition.

Examples of such dispersion stabilizers include esters of polyhydric alcohols such as glycerol, sorbitan, polyglycerol, and sucrose with higher carboxylic acids, and modified silicones containing small amounts of polar groups. Other commercially available dispersion stabilizers can also be used.

Various proposals have already been made as methods for dispersing the composition containing cellulose acetate into the dispersion medium, including a method that provides a wide range of particle size distributions and a method that provides a monodispersed particle size. One example of a method suitable for preparing a product with a uniform particle size is a method using an apparatus generally called a microreactor, in which the liquid dispersion medium is passed at an appropriate rate, while the homogeneous composition to form gel is injected through a finer nozzle.

Alternatively, the following various methods may be used, for example: a method in which the flowable homogeneous composition of the present invention is extruded into the dispersion medium through membranes of a fixed pore size; a method in which the flowable homogeneous composition of the present invention is placed in an inner cylinder provided with pores of a fixed size, and the inner cylinder is rotated in the dispersion medium, which causes the gelled homogeneous composition to be extruded by centrifugal force; a method in which the dispersion medium optionally containing a dispersion stabilizer and the flowable homogeneous composition are fed into a column packed with beads of a fixed size; a method in which the flowable homogeneous composition is injected into the dispersion medium through a vibration nozzle; and a method utilizing (ultra)sonic waves.

In the Examples, the simplest method that utilizes stirring and yet provides mixtures of various particle sizes will be described by way of example. In this method, the homogeneous composition is added to the dispersion medium, and then these components are mixed and stirred at the phase transition temperature or higher to produce substantially spherical particles composed of the composition. The substantially spherical particles are then cooled below the phase transition temperature, thereby gelling dispersion droplets of the homogeneous composition. The conditions for stirring and mixing may be selected as appropriate, depending on the intended average particle size.

Note that the temperature of the dispersion medium when the composition containing cellulose acetate is added to the dispersion medium may be a temperature at which the composition is maintained in liquid state. Specifically, in an exemplary embodiment, the temperature of the dispersion medium may be set higher than the range of temperatures where the composition undergoes the phase transition. Setting the temperature of the dispersion medium at such a temperature facilitates stirring and mixing of the composition. On the other hand, the temperature of the liquid to form gel and/or the dispersion medium at the time of addition of the composition does not need to be higher than or equal to the phase transition temperature. This is because even if the temperature of the flowable homogeneous composition has dropped below the phase transition temperature from a temperature higher than or equal to the phase transition temperature, a certain time is required until the composition forms a gel.

It is, however, preferred to add and disperse the homogeneous composition into the dispersion medium, while the homogeneous composition is retaining its flowability.

If this condition is not satisfied, the resulting particles will have an irregular broken shape, which is unsuitable for chromatographic purposes. Note, however, that after the composition in gel form is broken and dispersed, the gel may be melted once by increasing the temperature above the phase transition temperature, and then gelled again by reducing the temperature.

The composition is ultimately gelled by cooling the dispersion medium to a temperature lower than the range of temperatures where the composition undergoes the phase transition.

<Separating Solvent>

While the subsequent process is not particularly limited, in the Examples of the present invention, a separating solvent for extracting the gelled cellulose acetate from the dispersion medium may be used.

In an exemplary embodiment, for example, a separating solvent may be added into the dispersion medium in which the composition is dispersed, in order to separate, from the dispersion medium, only the cellulose acetate as gelled particles in the particles composed of the gelled composition.

The separating solvent to be used is a separating solvent that is not miscible with the dispersion medium, and is miscible with water and the organic solvent in the composition, although it does not dissolve the cellulose acetate contained in the gelled composition. This prevents re-dissolution of the cellulose acetate in the gelled composition.

Examples of such separating solvents include water, methanol, ethanol, 2-propanol, acetamide, formamide, and a mixture thereof.

While it is possible to directly filter off the cellulose acetate gel dispersed in the dispersion medium, this increases the risk of deformation or breakage of the gelled particles, because the dispersion medium, which generally has a high viscosity, is subjected to pressure during filtration. The pressure during filtration may be reduced by adding into the dispersion medium a low-viscosity liquid miscible with the dispersion medium.

Note that it is preferred to add into the separating solvent a reagent for decomposing the cellulose acetate into cellulose (deacetylation), for example, a metal hydroxide such as potassium hydroxide or sodium hydroxide, or a base such as an amine, to cause the deacetylation reaction for changing the cellulose acetate into cellulose in the separation step.

When the deacetylation reaction is not performed without adding a base into the separating solvent, the gelled particles composed of the cellulose acetate that have been separated may be extracted and then reacted with a base.

The porous cellulose particles after the deacetylation reaction are washed in an appropriate manner such as with water or the like, and are generally stored in a water-wet state. When drying the porous cellulose particles, an appropriate amount of a saccharide, glycerol, or the like is added. For long-term storage in a water-wet state, a preservative such as an alcohol or sodium azide is added to prevent corruption. Alternatively, the porous cellulose particles to which glycerol, a saccharide, urea, or the like has been added may be dried. For use, the porous cellulose particles are packed into a column in accordance with a conventional method.

Among the porous cellulose particles obtained using the method of the present invention, particles having a substantially spherical to spherical shape with a particle size (maximum size) of 30 to 300 µm may be screened in accordance with known appropriate classification, and used as a chromatographic packing material. An example of chromatography may be size exclusion chromatography. The fact that the porous cellulose particles can be used for size exclusion chromatography means that when the porous cellulose particles are bound with an appropriate ligand, they can also be used for chromatographic separation using various modes other than the size exclusion. Examples of such modes include ion exchange, hydrophobic, and affinity modes.

Figure 3:
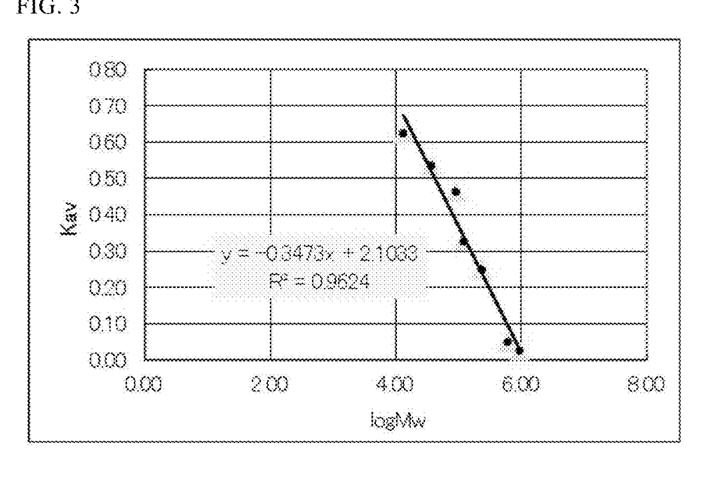
FIG. 3 is a diagram showing a calibration curve prepared by separating standard polyethylene oxide using the porous cellulose particles obtained in Example 1.

In general, for the separation and purification of biopolymers produced by biotechnology, such as hormones, enzymes, and antibody drugs, it is preferred to use a matrix having a pore size that allows sufficient entry of these substances. Specifically, when gel filtration chromatography is performed using a column packed with the porous cellulose particles, and using water as the mobile phase, fractionation is expected to occur in a certain region of molecular weights ranging from approximately $10^3$ to $10^7$ as converted into the molecular weights of polyethylene glycols. The elution of standard materials (polyethylene glycols) having molecular weights of $10^4$ to $10^6$ at different times by GPC in Example 1 shows that the pore size of the matrix that can be prepared using the method of the present invention is suitable for separation and purification of these materials. The pore size can be finely adjusted by changing the cellulose acetate concentration in the composition to be gelled which contains water, the organic solvent, and cellulose acetate, or depending on the gelling conditions (for example, by adjusting the rate of cooling of the homogeneous composition).

A method for preparing an adsorbent for use in the affinity mode will be described hereinafter.

A protein may be used as the affinity ligand. Examples of proteins that can be used in the present invention include substances having molecular weights of 3 to 300 kDa, and preferably 30 to 150 kDa, and having an affinity for the protein to be separated such as an antibody.

Among the above, protein A, protein G, protein L, and a functional variant thereof are preferred as the affinity ligand because of their high selectivity when used for separating a protein of an antibody.

For the principal purpose of separating an antibody, the ligand is preferably a ligand that can specifically bind to a portion of an immunoglobulin.

The above-described functional variant refers to a protein having at least one modification in a natural amino acid sequence, and still retaining at least one function accompanying the natural sequence. A natural sequence originally contains a naturally occurring amino acid sequence. Examples of alterations to the amino acids include the substitution of one or more amino acids with other amino acids, the deletion of one or more amino acids and/or the addition of one or more amino acids, and any combination thereof. In an exemplary embodiment, a combination of the addition, deletion, and substitution of amino acids may be made in the natural sequence. The functional variant may contain a fragment or domain of the protein. The amino acid sequence of the functional variant may be at least 70% identical, at least 75% identical, at least 80% identical, at least 85% identical, at least 90% identical, at least 95% identical, and at least 98% identical to the natural amino acid sequence, and still retains at least one function accompanying the natural sequence.

The amount of the protein supported on the porous cellulose particles is preferably 1.0 to 25 parts by weight based on 100 parts by weight of the porous cellulose particles.

Further, in an exemplary embodiment, the amount of the protein supported on the porous cellulose particles may be 1 to 50 mg per ml of the porous cellulose particles.

By further including the step of immobilizing the above-described affinity ligand into the method for producing the porous cellulose medium produced using the method of the present invention, an adsorbent to which the affinity ligand is bound can be produced.

This adsorbent can also be used for a separating agent for affinity chromatography.

An exemplary embodiment of the method for producing an adsorbent may be described as follows.

First, the method for producing an adsorbent may include the step of subjecting spherical particles of the porous cellulose medium produced using the above-described method to a cross-linking reaction using a cross-linking agent.

The cross-linking method is not particularly limited, and a cross-linking agent, for example, a halohydrin such as epichlorohydrin, epibromohydrin, or dichlorohydrin, bisoxirane, or polyoxirane, can be used.

Next, the method for producing an adsorbent may include the step of activating the cross-linked cellulose particles.

A known reactive functional group may be introduced to activate the cross-linked cellulose particles. When the cross-linked cellulose particles are activated using, for example, cyanogen bromide (CNBr), N,N'-disuccinimidyl carbonate (DSC), an epoxide, and an activated carboxylic acid (NHS ester), an original functional group of the porous cellulose particles can be replaced with a functional group more reactive with the compound to be immobilized as the ligand. Then, an adsorbent is produced by way of the subsequent step of immobilizing the ligand onto the porous cellulose particles by reacting the porous cellulose particles with the compound to be immobilized as the ligand.

As an alternative to the above-described method, a method for producing an adsorbent may be used in which condensation and cross-linking are performed by adding a condensation reagent such as carbodiimide or a reagent having a plurality of functional groups in the molecule such as glutaraldehyde, into the system containing the porous cellulose particles and the compound to be immobilized as the ligand, to thereby immobilize the ligand onto the porous cellulose particles.

In another exemplary embodiment of binding the porous cellulose particles with the affinity ligand, a formyl group may be introduced into the cellulose and the cellulose particles, and the formyl group may be reacted with an amino group of a protein.

The reaction of introducing a formyl group may be performed, for example, by oxidizing a polysaccharide having vicinal hydroxyl groups using a periodate oxidation method, and producing a formyl group on the sugar chain.

An alternative method may be used in which a formyl group is introduced through any of various spacers obtained by, for example, reacting a glyceryl group obtained by the ring opening of an epoxy group with a periodate. For example, an amino sugar such as glucosamine can be used as a spacer.

Then, the formyl group of the porous cellulose particles can be bound with a protein such as protein A, using a known method. In an exemplary embodiment, for example, the porous cellulose particles introduced via an amino sugar such as glucosamine as the spacer may be reacted with a solution containing protein A. An example of such a method is described in Japanese Patent Laid-Open No. 2008-279366.

<Monolith>

A monolith is an integral mass of a porous raw material. In chromatography using the above-described particulate packing material, although an eluent passes through even the micropores of the particles, it passes more through gaps between particles. In contrast, the monolith allows an eluent to pass through the micropores of the integral porous material. Therefore, typically, in the monolith, the solids content is made lower than that in the particulate packing material to reduce resistance to the flow of the eluent. The monolith, however, is completely identical to the packing material in terms of essential mechanism of separation, except for the case where it is used as a filtration material.

A method for producing a porous cellulose monolith of the present invention includes the steps of placing a flowable homogeneous composition containing cellulose acetate, an organic solvent, and water in a mold container, and gelling the homogeneous composition within the mold container through a decrease in temperature; and hydrolyzing the cellulose acetate contained in the resulting gel.

The same cellulose acetate and the organic solvent as those used for the preparation of the spherical particles can be used in this method.

In liquid chromatography, it is extremely important that an eluent pass at the same velocity in every portion of the separating agent, and a so-called piston flow be created. In the packing material, variations in the properties of individual particles are equalized by mixing, and thus, a certain degree of difference in the properties between particles is acceptable. It is, however, important for the packing material to have uniform gaps between particles, which plays a significant part in the liquid flow. To achieve this, the technique used in packing the packing material into a container called a column is a key factor.

In the monolith, on the other hand, it is extremely important that the resulting porous structure be homogeneous in a direction perpendicular to the flow of the eluent, and no gaps through which the liquid readily passes be formed between the monolith and the container. The porous material homogeneous in the perpendicular direction as referred to herein cannot be prepared through contact with a gelling agent (precipitant), or through evaporation of the solvent, which is a known technique.

The method of the present invention utilizing gelation of cellulose acetate upon a change in temperature is suitable for preparing the monolith, in that it can provide a homogeneous gel if the equalization of the temperature of the raw material composition is faster than the gelation rate.

The monolith is prepared as follows. The above-described homogeneous composition containing water, the organic solvent, and cellulose acetate is introduced into a mold container having a desired shape, and then a gel composed of the composition is formed by reducing the temperature thereof. After the gel is dried as is, or dried using an appropriate method, the cellulose acetate contained in the obtained gel is hydrolyzed. As the base and method used for hydrolysis, those used for the preparation of the spherical porous cellulose particles can be used.

In order to evaluate the prepared monolith, the monolith needs to be contained in an appropriate container such that no gaps are formed, or no local compaction is present, as described above. The method for achieving this may be either a known or unknown method. Generally, when the monolith is produced by gelation, it undergoes a certain shrinkage, resulting in gaps being formed between the container and the monolith. In this case, the monolith can be contained in the container without gaps being present therebetween, for example by preventing the formation of gaps by modifying the wall surface of the container into a chemical structure having a strong affinity for cellulosic substances (for example, by bonding cellulose to the surface), or by causing shrinkage or swelling of the gel through an environmental change, or by making the size of the container adjustable.

EXAMPLES

The present invention will be described hereinafter in more detail with reference to examples; however, the scope of the present invention is in no way limited to these examples only.

Example 1

1. Preparation of Cellulose Monoacetate Solution 14.70 g of cellulose diacetate (degree of acetylation: 54.75%, viscosity of a 6% acetone solution: 0.117 Pa·s (25° C.)) vacuum dried at 100° C. for 1 hour was dissolved in 78 mL of DMSO (GR grade from Tokyo Chemical Industry Co., Ltd.). 4.20 g of hydrazine monohydrate >98% (from Tokyo Chemical Industry Co., Ltd.) and 12.01 g of DMSO were weighed into a separate container and mixed, and then the whole quantity of the mixture was added dropwise to the cellulose diacetate solution obtained above and mixed so as not to leave sediment. This solution was kept at 70° C. for 17 hours to obtain a cellulose monoacetate solution. 12.1 g of water was added to 20.2 g of the resulting solution and thoroughly mixed, and the mixture was then immersed in a warm bath, and the temperature was gradually elevated and lowered. As a result, it was found that the mixture was a viscous but flowable transparent liquid at a temperature higher than 40 to 45° C., but became cloudy and lost its flowability below this temperature.

Figure 1:
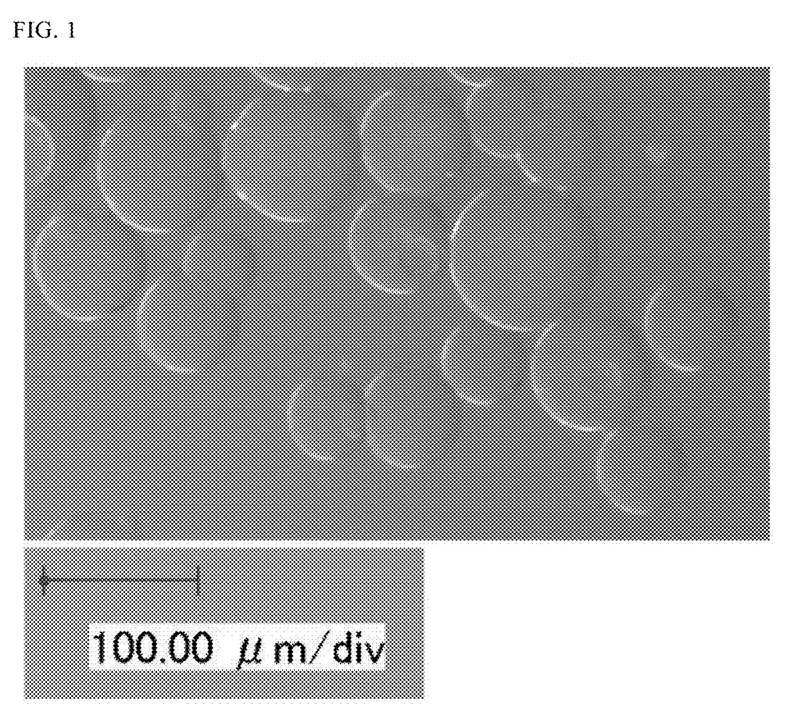
FIG. 1 is an optical micrograph of porous cellulose particles obtained using the method of the present invention (Example 1).
Figure 2:
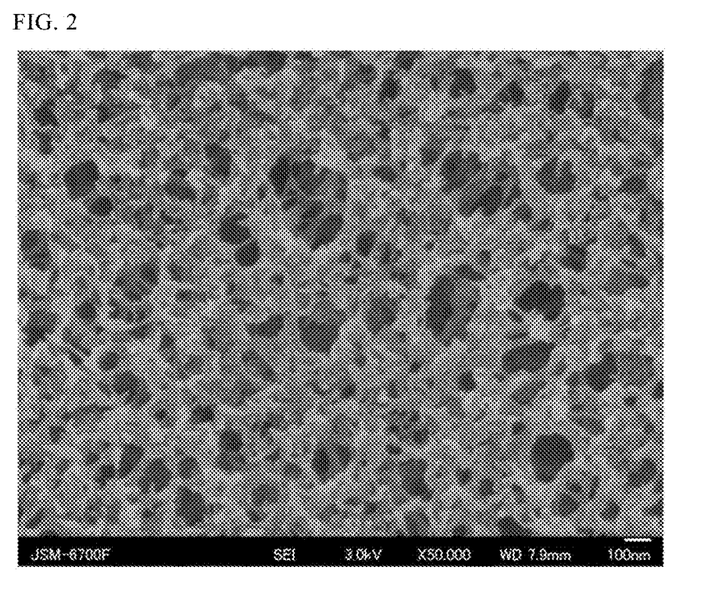
FIG. 2 is a scanning electron micrograph of the porous cellulose particles obtained using the method of the present invention (Example 1).

2. Preparation of Porous Cellulose Particles 154 g of a liquid paraffin (from Kanto Chemical Co., Inc., specific gravity: 0.87, Cica first grade) and 0.41 g of the emulsifier TSG10 (from Nihon Emulsion Co., Ltd.) were placed in a plastic (PE) container and kept at 70° C. in an oven. Meanwhile, 6.6 g each of water and the cellulose monoacetate solution prepared in section 1 above were thoroughly mixed at 60° C., and the mixture was cooled to room temperature, thus forming a cloudy jelly-like solid. This solid was introduced into the heated liquid paraffin described above and continued to be heated for 30 minutes, and then stirred at 950 to 1000 rpm for 5 minutes using an impeller with a diameter of 4 cm. The resulting dispersion was transferred into a 1 L beaker and cooled with water. After the dispersion was kept at 20° C. for 3 hours, a mixed solution of 0.75 g of potassium hydroxide, 20 g of water, and 150 mL of ethanol was added thereto and stirred slowly for 1 hour. After the mixture was allowed to stand overnight, sediment of white particles was observed at the bottom of the lower layer mainly composed of ethanol. FIG. 1 shows a micrograph of the sediment, which reveals that the sediment was substantially spherical in shape. Moreover, these particles were repeatedly washed with water, which was then replaced with tertiary butyl alcohol, and the particles were freeze-dried. An electron micrograph of the resulting particles shows that the particles had a porous surface (FIG. 2). Further, the washed particles were vacuum dried at 100° C., and an infrared absorption spectrum of the particles was measured by the KBr disk method. The infrared absorption spectrum showed no carbonyl stretching vibrations around $1720\ cm^{-1}$ derived from acetyl groups.

3. Size Exclusion Chromatography

Three batches of particles obtained as above were collected, and sized using a stainless screen while being dispersed in water, and portions of the particles ranging from 150 to 106 μm in size were collected. As a result, the sedimentation volume was about 10 mL. About 8 mL of the sediment was packed into columns with an inner diameter of 10 mm and a height of 100 mm, the samples of standard polyethylene oxide shown in Table 1 were injected into the columns, using pure water as the mobile phase, under the conditions summarized below, and the samples were detected with a differential refractometer detector. A calibration curve drawn in accordance with a conventional method is shown in FIG. 3.

Columns used:
HR 10/100 (GE Healthcare)
Tricorn 10/100 (GE Healthcare)
Flow rate: 0.05 ml/min (analysis time: 180-240 min)
◇ PEO
Eluent: ultrapure water (degassed)
Standard Materials (Type, Concentration, and Injection Volume)

TABLE 1

TSKgel Standard Polyethylene Oxide (purchased from Tosoh Corporation)

|  | Molecular weight | concn (mg/ml) |
|---|---|---|
| PEO | 940,000 | 5.0 |
| SE-150 | 610,000 | 5.0 |
| SE-70 | 240,000 | 5.0 |
| SE-30 | 120,000 | 5.0 |
| SE-8 | 92,000 | 5.0 |
| SE-5 | 37,000 | 5.0 |
| SE-2 | 13,000 | 5.0 |
| Blue dextran 2000 | 2,000,000 | 3.0 |

Inj volume 10 μL

Example 2

Preparation of Porous Cellulose Particles 16.27 g of VTR cellulose diacetate (degree of acetylation: 54.75%, viscosity of a 6% acetone solution: 0.117 Pa·s (25° C.)) was dissolved in 182.49 g of DMSO. 39.19 g of this solution was placed into a beaker, a mixed solution of 11.01 g of DMSO and 11.01 g of water was added while heating to 80° C., and the mixture was stirred. This gave a transparent viscous liquid, which formed a gel when allowed to cool to room temperature.

Meanwhile, 2.04 g of the emulsifier TSG10 (from Nihon Emulsion Co., Ltd.) was added to 750 mL of a liquid paraffin (from Kanto Chemical Co., Inc., Cica first grade), and the mixture was kept warm at 90° C. When the above-described gel was introduced into the mixture, the gel dissolved therein and accumulated in the lower layer. While a container containing this solution was immersed in a water bath at 80° C., a disperser with a diameter of 80 mm was inserted into the liquid contents, and the liquid contents were stirred under rotation at 400 rpm for 5 minutes. After the completion of stirring, the container was immersed in a water bath and cooled. After 3 hours, particulate matter and partially mass-like aggregates sedimented in the bottom of the container. A solution of 3.09 g of KOH dissolved in 50 mL of water was added thereto and mildly stirred at about 10 rpm. After the mixture was allowed to stand overnight, 400 mL of water was added and mildly stirred, and then the lower layer was separated. The separated lower layer was neutralized with a small amount of dry ice and then washed with water. Microscopic observation revealed that the resulting particles were spherical with a size of about 50 μm. An infrared spectrum of the particles did not show absorption around 1720 cm$^{-1}$ indicating the presence of the carbonyl group of the acetyl ester.

Example 3

Preparation of Porous Cellulose Particles 2.60 g of cellulose diacetate (degree of acetylation: 54.75%, viscosity of a 6% acetone solution: 0.117 Pa·s (25° C.)) was dissolved in 25.01 g of NMP (N-methylpyrrolidone) and 5.00 g of water. A mixed solution of 3.71 g of NMP and 3.70 g of water was added to this solution while heating to 55° C., and the mixture was stirred. This gave a transparent viscous liquid, which formed a gel upon cooling in an ice bath.

Figure 4:
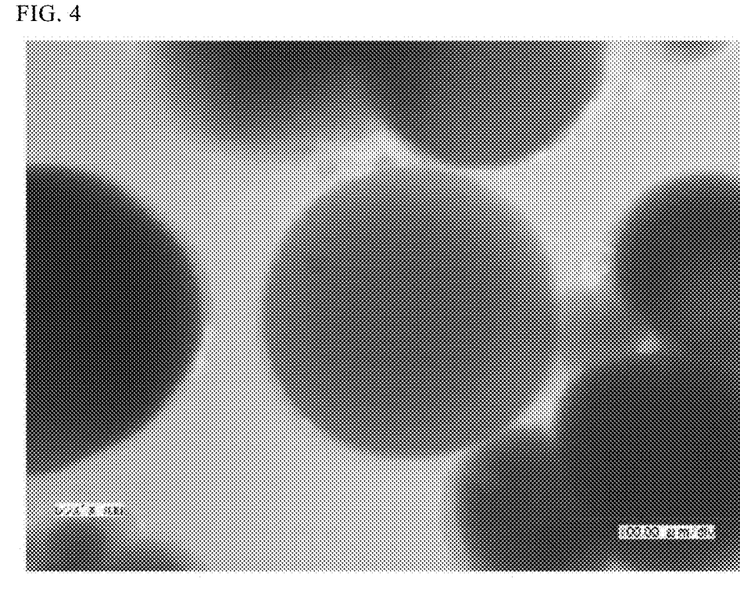
FIG. 4 is a scanning electron micrograph of porous cellulose particles obtained using the method of the present invention (Example 3).
Figure 5:
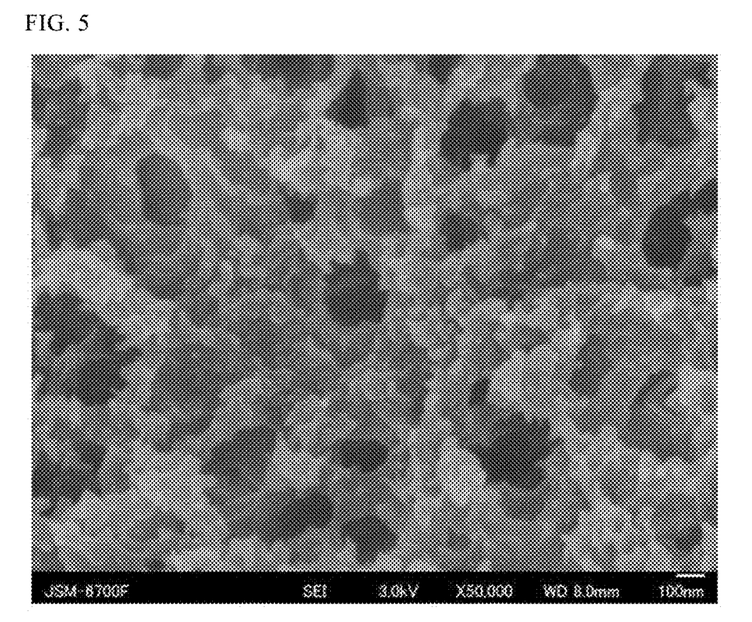
FIG. 5 is a scanning electron micrograph of porous cellulose particles obtained using the method of the present invention (Example 6).
Figure 6:
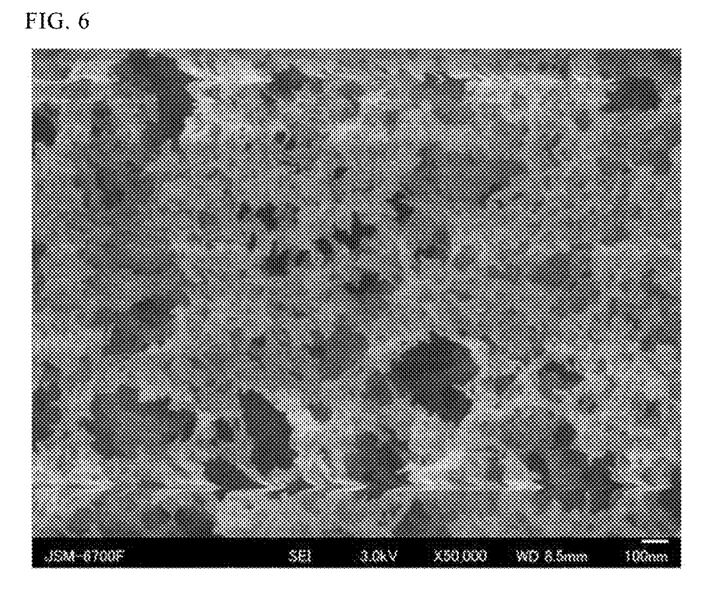
FIG. 6 is a scanning electron micrograph of porous cellulose particles obtained using the method of the present invention (Example 7).
Figure 7:
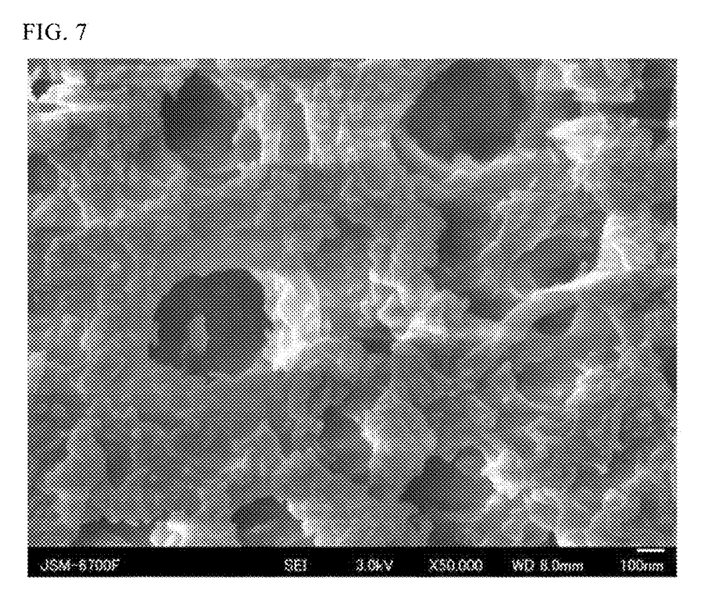
FIG. 7 is a scanning electron micrograph of porous cellulose particles obtained using the method of the present invention (Example 8).
Figure 8:
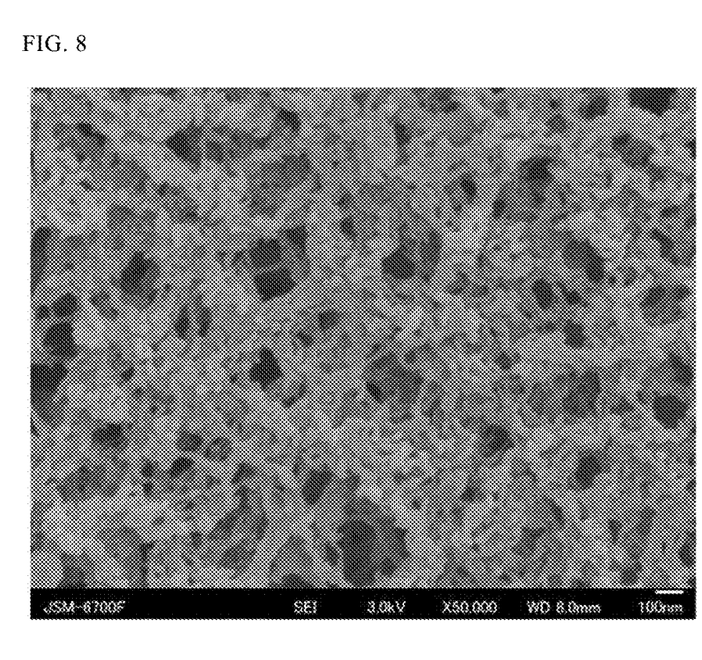
FIG. 8 is a scanning electron micrograph of porous cellulose particles obtained using the method of the present invention (Example 9).
Figure 9:
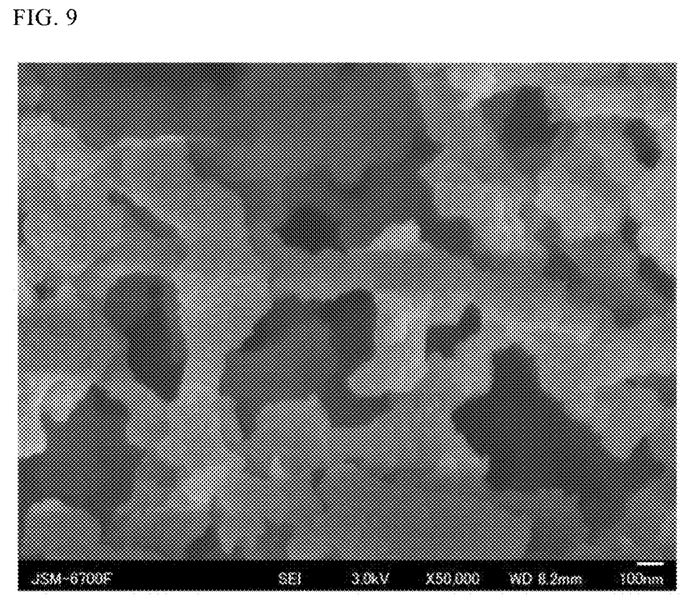
FIG. 9 is a scanning electron micrograph of porous cellulose particles obtained using the method of the present invention (Example 10).
Figure 10:
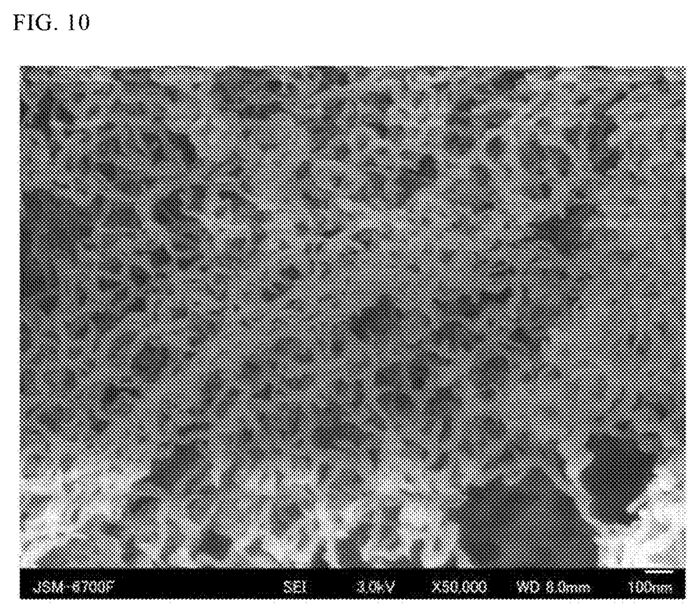
FIG. 10 is a scanning electron micrograph of porous cellulose particles obtained using the method of the present invention (Example 11).

Meanwhile, 0.64 g of the emulsifier TSG10 (from Nihon Emulsion Co., Ltd.) was added to 400 mL of a liquid paraffin (from Kanto Chemical Co., Inc., Cica first grade), and the mixture was kept warm at 55° C. When the above-described gel was introduced into the mixture, the gel dissolved therein and accumulated in the lower layer. While a container containing this solution was immersed in a water bath at 55° C., a disperser with a diameter of 80 mm was inserted into the liquid contents, and the liquid contents were stirred under rotation at 350 rpm for 10 minutes. After the completion of stirring, the container was immersed in a water bath and cooled. After 2 hours, particulate matter and partially mass-like aggregates sedimented in the bottom of the container. 200 mL of water was added thereto, and mildly stirred at about 10 rpm to separate the lower layer. Then, 200 mL of water was added, and this operation was repeated to extract the gel in the lower layer. 2.51 g of KOH was added thereto and mildly stirred, and after the mixture was allowed to stand for 2 nights, the supernatant was discarded. The residue was filtered off through a glass filter, and repeatedly washed with water. FIG. 4 shows a micrograph of the resulting particles, which reveals that the particles were substantially spherical in shape.

Example 4

Preparation of Porous Cellulose Diacetate Monolith

A glass vial with an inner diameter of 19 mm was filled with a composition containing 6.8 wt % of the same cellulose diacetate as that used in Example 1, 71.6 wt % of NMP (N-methylpyrrolidone), and 21.6 wt % of water, the composition was changed into a transparent solution at 60° C., and then the solution was allowed to cool to 15° C. After a night, the composition turned into a cloudy and opaque gel of the porous cellulose diacetate. As a result of repeatedly washing this gel with water, white columnar cellulose diacetate with a diameter of about 18 mm was obtained.

Preparation of Porous Cellulose Monolith 0.38 g of small pieces of the resulting porous cellulose diacetate monolith were immersed for a day and a night in a solution containing 0.2 g of potassium hydroxide, 1 mL of water, and 10 mL of ethanol, and then repeatedly washed with water. The resulting product shrank to about 85% its size before the potassium hydroxide treatment, but was white and showed no change in shape. Small pieces of this monolith were cut and rolled over filter paper to remove the water adhering to the surface. Then, the weight of the resulting product was measured and found to be 104.9 mg. This product was placed on a polystyrene weighing plate and dried in an oven at 90° C. for 1 hour. This resulted in shrunk semi-transparent solid small pieces having a weight of 9.9 mg, which, even after further continued drying, did not show a decrease in weight. Consequently, this monolith had a solids content of 9.4%. The dried monolith pieces were broken, and a very small amount of the broken pieces were molded into a disk together with potassium bromide in accordance with a routine method. An infrared absorption spectrum of the resulting product was measured, and no carbonyl stretching vibrations around 1720 cm$^{-1}$ derived from acetyl groups were observed, which revealed the conversion of the cellulose diacetate into cellulose.

Example 5

Preparation of Porous Cellulose Acetate Monolith and Cellulose Monolith

A porous cellulose acetate gel was obtained by applying the same operation as that in Example 4 to a composition containing 7.7 wt % of the same cellulose diacetate as that used in Example 1, 73.7 wt % of N,N-dimethylacetamide, and 18.6 wt % of water. This gel had a diameter of about 17 mm after being washed with water. Small pieces of this monolith were treated with potassium hydroxide under the same conditions as those used in Example 4 and washed with water. The resulting product shrank to 74% its original size, but was a white solid without any change in shape, and had a solids content of 12.7%. In the infrared absorption spectrum, no acetyl group was detected.

Example 6

1. Preparation of Porous Cellulose Particles 385 g of a liquid paraffin (from Kanto Chemical Co., Inc., specific gravity: 0.87, Cica first grade) and 2.05 g of the emulsifier TSG10 (from Nihon Emulsion Co., Ltd.) were placed in a 500 mL separable flask and kept at 60° C. in a water bath. Meanwhile, 16.5 g of the cellulose monoacetate solution prepared in Example 1-1, 3.5 g of DMSO, and 24.5 g of water were thoroughly mixed at 60° C. This mixture was introduced into the heated liquid paraffin described above and continued to be heated for 10 minutes, and then stirred at 250 rpm for 5 minutes using an impeller with a diameter of 6 cm. The resulting dispersion was transferred into a flat metal container and cooled with ice. After the dispersion was turned into a gel by being kept at 10° C. for 30 minutes, the gel was transferred into a 1 L Erlenmeyer flask, and 150 mL of heptane and a mixed solution of 1.9 g of potassium hydroxide, 20 g of water, and 150 mL of ethanol were added thereto and stirred slowly for 1 hour. After the mixture was allowed to stand overnight, water was added, and the lower layer containing gelled particles was separated and neutralized with the addition of acetic acid. Then, the resulting particles were washed with ethanol and water. Four batches of particles obtained as above were collected, and sized using a stainless screen while being dispersed in water, and portions of the particles ranging from 50 to 106 μm in size were collected. As a result, the sedimentation volume was about 10 mL.

2. Preparation of Cross-Linked Porous Cellulose Particles

To a 100 mL three-neck flask, a solution containing 7.9 mL of the porous cellulose particles obtained in Example 6-1 and 8.7 g of sodium sulfate dissolved in 23.6 g of water was added and stirred at 50° C. 0.48 g of a 45 wt % aqueous solution of sodium hydroxide and 75 mg of sodium borohydride were added and stirred. 4.86 g of the 45 wt % aqueous solution of sodium hydroxide and 4.98 g of epichlorohydrin were each added in seven equally divided amounts at intervals of 30 minutes over a period of approximately 3 hours. After the completion of the addition, the reaction was performed at 50° C. for 16 hours. After cooling to 40° C. or lower, 0.52 g of acetic acid was added for neutralization. The reaction mixture was filtered to collect the particles, and the particles were filtered and washed with pure water to obtain the intended cross-linked porous cellulose particles.

3. Immobilization of Protein a onto the Cross-Linked Porous Cellulose Particles and the Preparation of a Column The cross-linked porous cellulose particles obtained in Example 6-2 were filtered off through a glass filter, and washed with acetonitrile to obtain 3.3 mL of a support. The support was transferred into a flask, and 10 mL of an acetonitrile solution containing 2.5 mL of acetonitrile and 55 mg of di(N-succinimidyl) carbonate was added and shaken at 4° C. and 180 rpm. Next, 1 mL of an acetonitrile solution containing 41 mg of N,N-dimethylaminopyridine was added and reacted with shaking for 22 hours. The reaction mixture was filtered off through the glass filter and washed with 30 mL of acetonitrile, 30 mL of dioxane containing 5% acetic acid, 30 mL of methanol, and 30 mL of 2-propanol in this order to obtain an activated support. 1 mL of the activated support was taken into the glass filter and washed with a coupling buffer (0.1 M sodium phosphate, pH 7.0). The activated support was transferred into a flask, and 168 µL of a protein A-containing solution containing 53.6 mg/mL of protein A and 2 mL of the coupling buffer were added thereto and immobilized with shaking at 5° C. and 130 rpm for 22 hours. The resulting product was filtered off through the glass filter and washed with the coupling buffer. Measurement of the filtrate after the reaction using the Bradford method showed the immobilization of 9.0 mg of protein A per mL of the support. Next, the support was transferred into a flask, and 2 mL of 1M tris-hydrochloride (pH 8) was added to mask unreacted active groups by shaking at 25° C. and 130 rpm for 2 hours. The support was filtered off through the glass filter and washed alternately with a washing solution 1 (0.1 M tris-hydrochloride, 0.5 M sodium chloride, pH 8.0) and a washing solution 2 (0.1 M ammonium acetate buffer, 0.5 M sodium chloride, pH 4.0) for 3 cycles. 1 mL of the immobilized support was washed with pure water and packed into a Tricorn 5/50 Column. Additionally, a column was prepared in accordance with the same operation, using Sepharose 4 Fast Flow (GE Healthcare) (the amount of immobilized protein A: 10 mg/mL).

4. Antibody Adsorption Capacity of the Protein-Immobilized Column

Each of the protein A-immobilized columns prepared in Example 6-3 was placed on the liquid chromatography apparatus AKTAexplore (GE Healthcare Bioscience) and equilibrated by passing an adsorption buffer (20 mM phosphate buffer, 150 mM sodium chloride, pH 7.2) at 1 mL/min or 0.4 mL/min, and then human serum-derived γ-globulin (Wako Pure Chemical Industries, Ltd.) prepared at 1 mg/mL was injected. The injection was continued until 15% of the absorbance at 280 nm of the eluate was reached, and after washing with the adsorption buffer, the adsorption buffer was replaced with 20 mM citric acid (pH 2.4).

The dynamic adsorption capacity (DBC) was calculated based on the amount of the sample injected until the absorbance at 280 nm of the eluate excluding non-adsorbed components reached 10% of the absorbance of the injected sample. Table 2 shows the DBC for each of the immobilized columns.

TABLE 2

| Flow Rate | Protein A-Immobilized Cross-linked Porous Cellulose Particles | Protein A-Immobilized Sepharose 4 Fast Flow |
|---|---|---|
| 1.0 mL/min. | 10 mg | 8 mg |
| 0.4 mL/min. | 18 mg | 22 mg |

Example 7

Preparation of Porous Cellulose Particles 771 g of a liquid paraffin (from Kanto Chemical Co., Inc., specific gravity: 0.87, Cica first grade) and 4.11 g of the emulsifier TSG10 (from Nihon Emulsion Co., Ltd.) were placed in a 1 L separable flask and kept at 60° C. in a water bath. Meanwhile, 33 g of the cellulose monoacetate solution prepared in Example 1-1, 7 g of DMSO, and 49 g of water were thoroughly mixed at 60° C. This mixture was introduced into the heated liquid paraffin described above and continued to be heated for 10 minutes, and then stirred at 200 rpm for 10 minutes using an impeller with a diameter of 6 cm. The resulting dispersion was transferred into a flat metal container and cooled with water. After being cooled to 20° C. over a period of 15 minutes, the dispersion was further cooled to 10° C. over a period of 15 minutes while gradually adding ice into the water bath, to turn the dispersion into a gel. After the dispersion was kept at 10° C. for 30 minutes, the gel was transferred into a 2 L Erlenmeyer flask, and 200 mL of heptane and a mixed solution of 3.1 g of potassium hydroxide, 200 g of water, and 200 mL of ethanol were added thereto and stirred slowly for 1 hour to obtain particles. After the particles were allowed to stand overnight, water was added, and the lower layer containing gelled particles was separated and neutralized with the addition of acetic acid. Then, the resulting particles were washed with ethanol and water. The particles were sized using a stainless screen while being dispersed in water, and portions of the particles ranging from 50 to 106 µm in size were collected. As a result, the sedimentation volume was about 8 mL. A column was prepared by performing cross-linking and immobilization of protein A in accordance with the same operation as that in Example 6. The dynamic adsorption capacity of the prepared column was 7 mg at a flow rate of 1.0 mL/min and 18 mg at a flow rate of 0.4 mL/min.

Example 8

Preparation of Porous Cellulose Particles 13 g of a liquid paraffin (from Kanto Chemical Co., Inc., specific gravity: 0.87, Cica first grade) and 75 mg of the emulsifier TSG10 (from Nihon Emulsion Co., Ltd.) were placed in a 20 mL sample tube and kept at 60° C. in a water bath. Meanwhile, 1.65 g of the cellulose monoacetate solution prepared in Example 1-1, 0.35 g of DMSO, and 2.45 g of water were thoroughly mixed at 60° C. 1.5 g of this cellulose monoacetate solution was introduced into the heated liquid paraffin described above and continued to be heated for 5 minutes, and then stirred with manual shaking for 1 minute. The sample tube was cooled with ice and kept at 10° C. for 30 minutes to turn the dispersion into a gel. The gel was then transferred into a 100 mL Erlenmeyer flask, and 20 mL of heptane and a mixed solution of 0.1 g of potassium hydroxide, 1 g of water, and 20 mL of ethanol were added thereto and stirred slowly for 1 hour to obtain particles. After the particles were allowed to stand overnight, water was added and particles at the lower layer were separated, and the particles were washed with ethanol and water.

Example 9

Preparation of Porous Cellulose Particles 13 g of a liquid paraffin (from Kanto Chemical Co., Inc., specific gravity: 0.87, Cica first grade) and 75 mg of the emulsifier TSG10 (from Nihon Emulsion Co., Ltd.) were placed in a 20 mL sample tube and kept at 60° C. in a water bath. Meanwhile, 1.65 g of the cellulose monoacetate solution prepared in Example 1-1, 0.35 g of DMSO, and 2.45 g of water were thoroughly mixed at 60° C. 1.5 g of this cellulose monoacetate solution was introduced into the heated liquid paraffin described above and continued to be heated for 5 minutes, and then stirred with manual shaking for 1 minute. After the sample tube was cooled with water to 20° C. over a period of 15 minutes, the dispersion was further cooled to 10° C. over a period of 15 minutes while gradually adding ice into the water bath. The sample tube was kept at 10° C. for 30 minutes to turn the dispersion into a gel. The gel was then transferred into a 100 mL Erlenmeyer flask, and 20 mL of heptane and a mixed solution of 0.1 g of potassium hydroxide, 1 g of water, and 20 mL of ethanol were added thereto and stirred slowly for 1 hour to obtain particles. After the particles were allowed to stand overnight, water was added and particles at the lower layer were separated, and the particles were washed with ethanol and water.

Example 10

Preparation of Porous Cellulose Particles

Porous cellulose particles were prepared in accordance with the same operation as that in Example 9, except that DMSO in the cellulose monoacetate solution used in Example 9 was changed to NMP (N-methylpyrrolidone).

Example 11

Preparation of Porous Cellulose Particles

Porous cellulose particles were prepared in accordance with the same operation as that in Example 9, except that DMSO in the cellulose monoacetate solution used in Example 9 was changed to N,N-dimethylacetamide.

INDUSTRIAL APPLICABILITY

In accordance with the method for producing a porous cellulose medium of the present invention, a porous cellulose medium is produced by utilizing the property of a specific composition containing cellulose acetate to form a gel upon a change in temperature.

In the gelation process of cellulose acetate, the pore size becomes uniform. This differs from conventional methods for producing porous cellulose media in which the solvent is evaporated during the process of pore formation, which causes migration of substances. Further, in accordance with the method of the present invention, the size of the pores of the obtained porous cellulose medium is as large as approximately several thousands of angstroms. The hardness of the porous cellulose medium obtained using the method of the present invention is approximately equal to those of conventionally available commercial products. The porous cellulose medium obtained using the method of the present invention, either in the form of spherical particles or a monolith, is useful as a separating agent.

The invention claimed is:

1. A method for producing a porous cellulose medium comprising the steps of:
   gelling a flowable homogeneous composition comprising cellulose acetate, an organic solvent, and water through a decrease in temperature; and
   hydrolyzing the cellulose acetate contained in the resulting gel;
   wherein the method does not comprise adding a reagent for inducing gelation to the composition; and
   wherein the homogeneous composition has, in a range of temperatures from 0° C. to 100° C., a temperature range where the homogeneous composition is a transparent flowable liquid, and a phase transition temperature at which the homogeneous composition loses flowability at a temperature lower than the temperature range.

2. The method for producing porous cellulose medium according to claim 1, wherein the gelation is induced by a change in temperature, without the addition of a reagent for inducing gelation.

3. A method for producing spherical porous cellulose particles comprising:
   a first step of obtaining a dispersion by dispersing a flowable homogeneous composition comprising cellulose acetate, an organic solvent, and water in a dispersion medium not miscible with the homogeneous composition;
   a second step of forming gelled particles composed of the composition by gelling the composition by reducing a temperature of the resulting dispersion; and
   a third step of hydrolyzing the cellulose acetate contained in the resulting gelled particles;
   wherein the method does not comprise adding a reagent for inducing gelation to the composition; and
   wherein the homogeneous composition has, in a range of temperatures from 0° C. to 100° C., a temperature range where the homogeneous composition is a transparent flowable liquid, and a phase transition temperature at which the homogeneous composition loses flowability at a temperature lower than the temperature range.

4. The method for producing spherical porous cellulose particles according to claim 3, which comprises, between the second step and the third step, the step of adding a separating solvent for separating the resulting gelled particles, into the dispersion in which the gelled particles are formed, thereby separating the gelled particles into the separating solvent.

5. The method for producing spherical porous cellulose particles according to claim 4, wherein the separating solvent is water, methanol, ethanol, 2-propanol, acetamide, formamide, or a mixture thereof.

6. The method for producing spherical porous cellulose particles according to claim 5, wherein a dispersion stabilizer is added into the dispersion medium.

7. The method for producing spherical porous cellulose particles according to claim 6, wherein the dispersion medium is a hydrocarbon having 20 or more carbon atoms, a silicone oil, or a fluorinated hydrocarbon.

8. The method for producing spherical porous cellulose particles according to claim 3, wherein the gelation is induced by a change in temperature, without the addition of a reagent for inducing gelation.

9. A method for producing an adsorbent comprising the step of:
  immobilizing an affinity ligand onto the porous cellulose medium obtained using the method according to claim 1 or the spherical porous cellulose particles obtained using the method according to claim 3.

10. The method for producing an adsorbent according to claim 9, wherein the affinity ligand is one or more selected from the group consisting of protein A, protein G, protein L, and a functional variant thereof.

11. A method for purifying a target substance comprising:
  a first step of contacting the adsorbent obtained using the method according to claim 10 with a mixture comprising the target substance to allow the target substance to bind to the affinity ligand immobilized onto the adsorbent; and
  a second step of separating the target substance bound to the affinity ligand on the adsorbent.

\* \* \* \* \*